United States Patent [19]

Tsukada et al.

[11] 4,409,233

[45] Oct. 11, 1983

[54] HIGHLY CONCENTRATED PREPARATIONS OF DOPA COMPOUNDS

[75] Inventors: Kazuhiro Tsukada; Wataru Kato, both of Hiromachi, Japan

[73] Assignee: Sankyo Company, Limited, Tokyo, Japan

[21] Appl. No.: 262,065

[22] PCT Filed: Jul. 2, 1979

[86] PCT No.: PCT/JP79/00174

§ 371 Date: Mar. 4, 1980

§ 102(e) Date: Sep. 17, 1979

[30] Foreign Application Priority Data

Jul. 4, 1978 [JP] Japan ................................. 53-81285

[51] Int. Cl.³ ............................................ A01N 37/13
[52] U.S. Cl. .............................. 424/273 R; 424/274; 424/319

[58] Field of Search ............ 562/460; 424/319, 273 R, 424/274

[56] References Cited

U.S. PATENT DOCUMENTS 3,911,137 10/1975 Miki et al. ............................ 424/319
4,321,264 3/1982 Vickers .............................. 424/319

*Primary Examiner*—Bernard Helfin
*Attorney, Agent, or Firm*—Frishauf, Holtz, Goodman & Woodward

[57] ABSTRACT

A highly concentrated aqueous composition of a dopa which comprises a dopa and at least one amino acid selected from the group consisting of methionine, proline, hydroxyproline, serine, threonine, valine, arginine, lysine, histidine and ornithine. Said composition having a concentration of said amino acid of 1–300 mg per ml of said aqueous solution of a dopa compound.

16 Claims, No Drawings

HIGHLY CONCENTRATED PREPARATIONS OF DOPA COMPOUNDS

TECHNICAL FIELD

This invention relates to a process for preparing a highly concentrated preparation of dopas known as a remedy for Parkinson's disease or a hypotensive agent.

BACKGROUND ART

Typical examples of a dopa include dopa [β-(3,4-dihydroxyphenyl)-α-alanine] and methyldopa [L-3-(3,4-dihydroxyphenyl)-2-methylalanine]. The former is known as a remedy for Parkinson's disease and the latter is known as a hypotensive agent. These compounds, however, have poor solubility in water and are inconvenient to be used in the form of a solution, particularly an injection. For example, the solubility of dopa in water is 2.5 mg/ml and 20 ml of water is necessary to dissolve the minimal dose (50 mg of dopa). Such circumstances require large ampules which are inconvenient for use. Therefore, preparations containing these compounds at a high concentration have been desired. Heretofore, there have been known attempts for the preparation of a highly concentrated dopa preparation; U.S. Pat. Nos. 3,916,004 and 3,911,137. The former comprises reacting a dopa with a non-toxic polyvalent metal salt to form a complex and the latter comprises adding a high molecular weight compound to a dopa to dissolve the dopa at a high concentration. However, the concentration of the dissolved dopa in these two inventions has not yet been sufficient to meet the requirement in the pharmaceutical field and there has been a demand for a process for preparing a much more highly concentrated dopa preparation. This invention provides a process for preparing a far more highly concentrated dopa preparation than made in a prior art. Also, another object of this invention is to provide a highly concentrated preparation of a dopa compound in the form of an aqueous solution or a freeze-dried preparation thereof.

DISCLOSURE OF INVENTION

As a result of further studies to dissolve a dopa compound in water at a high concentration, the present inventors have found that a dopa can be dissolved in a high concentration (10–100 mg/ml) by adding a basic amino acid and/or a certain type of a neutral amino acid to the dopa compound and also that a freeze-dried preparation of the highly concentrated solution thus prepared can be readily redissolved in distilled water for injection when used to reproduce the original high concentration of a dopa compound and can be kept stable at room temperature or even in a cold place. The present invention has been completed upon the above-mentioned findings. Thus, the present highly concentrated preparation of a dopa may be formulated and used in the form of an aqueous solution or a freeze-dried preparation therefrom. The basic amino acid which may be employed in this invention is not critical and may be any type and sort of the basic amino acids now available. Preferable examples thereof may include arginine, lysine, histidine and ornithine.

The neutral amino acid which may be employed in this invention is methionine, proline, hydroxyproline, serine, threonine or valine. In view of solubility, stability and the like, arginine, lysine, ornithine, methionine, serine, proline, hydroxyproline, threonine and valine are preferable. Also, these amino acids may be used alone or in combination of two or more thereof. A concentration of the amino acid to be added is dependent upon solubility of the additive, but 1–300 mg/ml is effective. Excessively high concentrations of the amono acid may cause coloration. In order to stabilize the active ingredient (a dopa), it is preferred to incorporate ascorbic acid or sulfites into the preparation of this invention. Furthermore, in the case of an injectable preparation, such additives as an isotonic agent, an antiseptic agent or a preservative commonly employed in an injectable preparation may be optionally added to the preparation of this invention, examples of such additives being sodium chloride, methylparaben, propylparaben, benzethonium chloride, benzalkonium chloride and the like.

Moreover, a far more highly concentrated preparation of a dopa (at 50 mg/ml) can be produced by the use of the amono acid in combination with gelatin, methyl cellulose and the like (U.S. Pat. No. 3,911,137) or a dextran, e.g., dextran 40, glucose and the like, as shown in the under-mentioned Example 10.

BEST MODE OF CARRYING OUT INVENTION

The following examples are given for the purpose of illustrating the present invention in more detail.

EXAMPLE 1

In 70 ml of distilled water for injection are dissolved successively 400 mg of sodium hydrogensulfite as a stabilizer and 20 mg of benzethonium chloride as a preservative. 2.0 g of dopa and 2.0 g of arginine are added to the solution, which is adjusted to pH 9.5 by addition of a sodium hydroxide solution under stirring. Distilled water for injection is added to the resulting solution to obtain 100 ml of a high concentration dopa solution (20 mg/ml). The solution is filtered aseptically by conventional means. The filtrate is poured into vials and lyophilized to afford a freeze-dried preparation for injection, which may be dissolved in distilled water for injection, when used, to give a clear solution containing dopa at a high concentration (20 mg/ml) (The solubility of dopa in water is 2.5 mg/ml.).

EXAMPLE 2

The freeze-dried preparation for injection is obtained following the same procedure as in Example 1, but replacing arginine with lysine.

EXAMPLE 3

The freeze-dried preparation for injection is obtained following the same procedure as in Example 1, but replacing arginine with ornithine.

EXAMPLE 4

The freeze-dried preparation for injection is obtained following the same procedure as in Example 1, but replacing arginine with methionine.

EXAMPLE 5

The freeze-dried preparation for injection is obtained following the same procedure as in Example 1, but replacing arginine with serine.

EXAMPLE 6

The freeze-dried preparation for injection is obtained following the same procedure as in Example 1, but replacing arginine with proline.

EXAMPLE 7

The freeze-dried preparation for injection is obtained following the same procedure as in Example 1, but replacing arginine with hydroxyproline.

EXAMPLE 8

The freeze-dried preparation for injection is obtained following the same procedure as in Example 1, but replacing arginine with threonine.

EXAMPLE 9

The freeze-dried preparation for injection is obtained following the same procedure as in Example 1, but replacing arginine with valine.

EXAMPLE 10

In 50 ml of distilled water for injection are dissolved 10 g of dextran 40, 400 mg of sodium hydrogensulfite and 20 mg of benzethonium chloride. To the resulting solution is added a solution of 10 mg of gelatin (dissolved by heating) in 20 ml of distilled water for injection. 5.0 g of dopa and 5.0 g of arginine are added to the solution, which is adjusted to pH 9.5 by addition of a sodium hydroxide solution under stirring. Distilled water for injection is added to the resulting solution to obtain 100 ml of a high concentration dopa solution of 50 mg/ml. The solution is treated in the same manner as in Example 1 to obtain a freeze-dried preparation for injection, which may be dissolved in distilled water for injection, when used, to give a clear solution containing dopa at a high concentration of 50–100 mg/ml.

INDUSTRIAL UTILIZABILITY

This invention is a superior technique for preparing a highly concentrated dopa preparation, especially an injectable preparation and a freeze-dried preparation for injection, in a pharmaceutical industry.

We claim:

1. A highly concentrated aqueous composition of a dopa which comprises a dopa and at least one amino acid selected from the group consisting of methionine, proline, hydroxyproline, serine, threonine, valine, arginine, lysine, histidine and ornithine, said composition having a concentration of said amino acid of 1–300 mg per ml of said aqueous composition.
2. The composition of claim 1 wherein said dopa is L-3-(3,4-dihydroxyphenyl)-2-methylalanine.
3. The composition of claim 1 wherein said dopa is $\beta$-(3,4-dihydroxyphenyl)-$\alpha$-alanine.
4. The composition of claim 3 wherein said amino acid is arginine.
5. The composition of claim 3 wherein said amino acid is lysine.
6. The composition of claim 3 wherein said amino acid is histidine.
7. The composition of claim 3 wherein said amino acid is ornithine.
8. The composition of claim 2 wherein said amino acid is arginine.
9. The composition of claim 2 wherein said amino acid is lysine.
10. The composition of claim 2 wherein said amino acid is histidine.
11. The composition of claim 2 wherein said amino acid is ornithine.
12. The composition of claim 1 wherein said amino acid is arginine.
13. The composition of claim 1 wherein said amino acid is lysine.
14. The composition of claim 1 wherein said amino acid is histidine.
15. The composition of claim 1 wherein said amino acid is ornithine.
16. A freeze-dried composition of a dopa which comprises a dopa and at least one amino acid selected from the group consisting of methionine, proline, hydroxyproline, serine, threonine, valine, arginine, lysine, histidine and ornithine, said composition having been prepared by freeze-drying a concentrated aqueous composition comprising said dopa and said amino acid in an amount of 1–300 mg per ml of said aqueous composition.

* * * * *